United States Patent [19]
Masters

[11] Patent Number: 6,017,312
[45] Date of Patent: Jan. 25, 2000

| [54] | MULTI-CHANNEL ROTARY TRANSFORMER |
|---|---|
| [75] | Inventor: Donald Masters, Sunnyvale, Calif. |
| [73] | Assignee: Boston Scientific Corporation, Maple Grove, Minn. |
| [21] | Appl. No.: 09/017,583 |
| [22] | Filed: Feb. 3, 1998 |
| [51] | Int. Cl.⁷ ...................................................... A61B 8/12 |
| [52] | U.S. Cl. .......................................................... 600/462 |
| [58] | Field of Search .................................. 600/437, 439, 600/444–446, 462–463, 471; 73/631–632; 336/120 |

[56] References Cited

U.S. PATENT DOCUMENTS

| 3,938,502 | 2/1976 | Bom ............................................. 128/2 |
|---|---|---|
| 4,149,419 | 4/1979 | Connell, Jr. et al. ...................... 73/621 |
| 4,155,259 | 5/1979 | Engeler ....................................... 73/626 |
| 4,674,515 | 6/1987 | Andou et al. ............................ 600/463 |
| 4,794,931 | 1/1989 | Yock .................................... 128/660.03 |
| 5,095,911 | 3/1992 | Pomeranz ............................ 128/662.06 |
| 5,108,411 | 4/1992 | McKenzie ................................ 606/159 |
| 5,156,154 | 10/1992 | Valenta, Jr. et al. ............... 128/661.09 |
| 5,168,878 | 12/1992 | Takano ................................ 128/662.06 |
| 5,188,106 | 2/1993 | Nappholz et al. ....................... 128/419 |
| 5,203,338 | 4/1993 | Jang .................................... 128/662.06 |
| 5,217,456 | 6/1993 | Narciso, Jr. ................................ 606/15 |
| 5,313,950 | 5/1994 | Ishikawa et al. ........................ 600/463 |
| 5,348,017 | 9/1994 | Thornton et al. .................... 128/662.06 |
| 5,429,136 | 7/1995 | Milo et al. ........................... 128/660.03 |
| 5,437,282 | 8/1995 | Koger et al. ......................... 128/662.06 |
| 5,503,155 | 4/1996 | Salmon et al. ...................... 128/662.06 |
| 5,544,660 | 8/1996 | Crowley ................................... 600/463 |
| 5,549,108 | 8/1996 | Edwards et al. ......................... 128/642 |
| 5,558,092 | 9/1996 | Unger et al. ........................ 128/660.03 |
| 5,590,653 | 1/1997 | Aida et al. ............................ 128/653.2 |
| 5,598,845 | 2/1997 | Chandraratna et al. ........... 128/662.03 |
| 5,620,417 | 4/1997 | Jang et al. ................................. 604/96 |

FOREIGN PATENT DOCUMENTS

0754430A2  6/1996  European Pat. Off. .

OTHER PUBLICATIONS

Roy W. Martin et al., "Design characteristics for intravascular ultrasonic catheters," *International Journal of Cardiac Imaging 4*, pp. 201–216, 1989.

M. Arditi et al., "An Annular Array System for High Resolution Breast Echography," *Ultrasonic Imaging 4*, pp. 1–31, 1982.

R. B. Bernardi et al., "A Dynamically Focused Annular Array," 1976 Ultrasonics Symposium Proceedings, pp. 157–159.

*Primary Examiner*—Francis J. Jaworski
*Attorney, Agent, or Firm*—Townsend and Townsend and Crew LLP

[57] ABSTRACT

The present invention provides for catheter systems and methods of their use. In one embodiment, the invention provides a catheter comprising a catheter body having a proximal end, a distal end and a working lumen. A drive cable is disposed within the lumen and at least one transducer is attached to the cable near the distal end. A rotary transformer is included, comprising a transformer stator which is spaced apart from a transformer rotor. The rotor is operably attached to the cable to rotate therewith. The rotor is electrically coupled to the transducer and is magnetically coupled to the stator to allow a signal to be transmitted from the transducer to the stator during rotation of the cable.

35 Claims, 8 Drawing Sheets

MULTI-CHANNEL ROTARY TRANSFORMER

BACKGROUND OF THE INVENTION

The present invention relates generally to the field of medical catheters, and in particular, to ultrasonic imaging medical catheters.

In recent years, the use of ultrasound systems for medical diagnostics has continued to grow. Ultrasonic systems are used in a plethora of medical fields and in a wide ranging number of diagnostic areas. As the desire to use ultrasonic imaging systems has grown, so has the level of sophistication of those systems.

To assist physicians and staff in performing diagnostic and therapeutic procedures, a number of ultrasonic imaging systems have been designed for use with catheters. In general, these systems comprise a single transducer element, frequently made of piezoelectric material, attached to the distal portion of an imaging catheter. Depending upon the procedure to be performed, the imaging catheter is inserted into the patient and the transducer is positioned within the patient to image a desired region of the patient's anatomy.

Many single transducer imaging catheters rotate the transducer in the distal end of the catheter in order to receive an image of a desired region. To receive images from the transducer, a transmission line is connected to the transducer, run the length of the catheter and connected to electronics used for displaying the images. Since the transducer and transmission line are rotated at a high rate of speed, the imaging catheters need to provide a means to transfer the transducer signal from a moving transmission line to a stable platform in order for the attached imaging system to produce a useable image. In order to accomplish this connection, many systems use some combination of springs, contact wires, slip rings or commutators in order to make physical contact with the rotating transmission lines. While generally successful in allowing the transducer-produced image to be received by the imaging equipment, such contacts, slip rings and the like tend to introduce noise and other interference which can detrimentally affect the electrical signals. Such components also are subject to wear and possible breakage due to the frictional contact between a moving part and a stationary part.

It would be preferable, therefore, to provide a method for transferring electrical signals from the transducer to the imaging equipment in a manner which reduces the chance of signal distortion or interference. It also would be desirable to provide a reusable system that does not rely solely on physical connections to transmit a signal. It would be further desirable to allow signals from a plurality of transducers to be received by the same imaging equipment. It also would be desirable to provide such a system for use with an ultrasonic imaging catheter.

SUMMARY OF THE INVENTION

The present invention provides for catheter systems and methods of their use. In one aspect, the invention provides a catheter comprising a catheter body having a proximal end, a distal end and a working lumen. A drive cable is disposed within the lumen and at least one transducer is attached to the cable near the distal end. A rotary transformer is also provided which comprises a transformer stator that is spaced apart from a transformer rotor. The rotor is operably attached to the cable to rotate therewith. The rotor is electrically coupled to the transducer and is magnetically coupled to the stator to allow a signal to be transmitted from the transducer to the stator during rotation of the cable.

In one aspect, the rotary transformer further comprises a plurality of rotor coils mounted in a plurality of concentric slots on a stator-facing side of the rotor. The rotor coils are coupled to the transducer and are disposed to face a plurality of stator coils mounted in a plurality of concentric slots located on a rotor-facing side of the stator. In this manner, the rotor coils and stator coils are magnetically coupled.

In one aspect, the stator-facing side of the rotor is a distal side of the rotor and the rotor-facing side of the stator is a proximal side of the stator. Alternatively, the stator-facing side of the rotor is a proximal side of the rotor and the rotor-facing side of the stator is a distal side of the stator.

In another aspect, the catheter system further includes a rotary shaft and a drive motor assembly. The rotary shaft couples the rotor to the drive motor assembly such that the drive motor assembly rotates the rotary shaft to in turn rotate the rotor.

In a further aspect of the invention a proximal end of the drive cable is operably attached to the rotary shaft. In this manner, rotation of the rotary shaft rotates the drive cable.

In another aspect, the catheter further comprises a transmission line having a proximal end and a distal end. The distal end is operably attached to the transducer and the proximal end is operably attached to the rotary transformer to allow the signal to be transmitted from the transducer to the transformer. In one aspect the transmission line comprises a coaxial cable. Alternatively, the transmission line may comprise a twisted pair cable.

In another aspect of the catheter system, the rotor further comprises an amplifier operably attached between the proximal end of the transmission line and the rotor coils. In this manner, signals transferred from the transducer are amplified before reaching the rotor coils.

In an alternative aspect, the stator further comprises an amplifier operably attached to the stator coils. Since the proximal end of the transmission line is operably attached to the rotor coils, signals from the transducer reach the rotor coils before being amplified.

In another aspect, the catheter further comprises a plurality of transducers and a plurality of transmission lines each having a proximal end and a distal end. Each transducer is operably attached to the distal end of one of the transmission lines and the proximal ends of the transmission lines are operably attached to the rotor.

In a still further aspect, a plurality of amplifiers are operably attached to the rotor coils such that each transducer is operably attached to the distal end of one of the transmission lines and the proximal end of each transmission line is operably attached to one of the amplifiers.

The invention further provides a rotary transformer system for use in a catheter system. The transformer system comprises a transformer stator operably attached to a transformer housing. A transformer rotor is provided which is adapted to be operably attached to a catheter. The rotor is operably attached to a rotary shaft such that the rotor is disposed to face the stator. A plurality of concentric slots located on a rotor-facing side of the stator are disposed to face a plurality of concentric slots on a stator-facing side of the rotor. A plurality of coils are mounted in the concentric slots on the stator and the rotor, wherein the coils mounted on the stator are magnetically coupled to the coils mounted on the rotor.

In one aspect, the stator-facing side of the rotor is a proximal side of the rotor and the rotor-facing side of the stator is a distal side of the stator. Alternatively, the stator-facing side of the rotor is a distal side of the rotor and the rotor-facing side of the stator is a proximal side of the stator.

In one aspect, the rotor and the stator each comprise ferrite. In another aspect, the coils comprise copper wires. In a further aspect, the rotor is rotatable relative to the stator to allow a communications signal to be transferred across a gap between the rotor and the stator during rotation of the rotor.

The invention also provides a method for imaging a body lumen. The method includes the step of providing a catheter comprising a catheter body having a proximal end, a distal end and a working lumen. A drive cable is disposed within the lumen and at least one transducer is attached to the cable near the distal end. A proximal end of the drive cable is operably attached to a rotary transformer. The catheter is coupled to a controller, and the catheter is introduced into a patient to position the transducer within a body lumen. The transducer is rotated by rotating the cable, and energizing the transducer occurs. The transducer captures a reflected signal and the reflected signal is transmitted across the transformer and to the controller. The method includes producing an image of the body lumen based on the reflected signal.

In one aspect of the method, the reflected signal is transmitted from the transducer to the transformer along a transmission line. In one aspect, the transmission line comprises a coaxial cable or a twisted pair cable.

In a further aspect of the method, the energizing step comprises transmitting an energizing signal across the transformer to the transducer. In another aspect, the rotary transformer comprises a transformer stator and a transformer rotor. The rotor is rotated relative to the stator while the reflected signal is transferred across a gap between the rotor and the stator.

In one aspect, the rotary transformer further comprises a plurality of coils mounted in a plurality of concentric slots on a proximal side of the rotor. The coils are disposed to face a plurality of coils mounted in a plurality of concentric slots located on a distal side of the transformer stator.

In another aspect, the rotary transformer further comprises a plurality of coils mounted in a plurality of concentric slots on a distal side of the rotor. The coils are disposed to face a plurality of coils mounted in a plurality of concentric slots located on a proximal side of the transformer stator.

In one aspect, the rotor further comprises an amplifier operably attached between the proximal end of the transmission line and the rotor coils. In this manner, the reflected signal is amplified before it is transferred across the gap between the rotor and the stator.

In still another aspect, the catheter further comprises a plurality of transducers and a plurality of transmission lines having proximal ends and distal ends. Each transducer is operably attached to the distal end of one of the transmission lines and the proximal ends of the transmission lines are operably attached to the rotary transformer. The transmitting step comprises transmitting a plurality of reflected signals across the rotary transformer to produce a plurality of images.

DESCRIPTION OF THE PREFERRED EMBODIMENT

The present invention provides for catheter systems and methods for their use. More specifically, the present invention incorporates a rotary transformer into a catheter system. Although useful with a wide variety of imaging catheters, including single transducer imaging catheters, the rotary transformer of the present invention will find its greatest use with catheters employing an annular array or other multi-transducer structures. For example, the multi-transducer transducer catheter disclosed in copending U.S. patent application Ser. No. 09/017,581 (attorney reference number 12553-006300, filed contemporaneously herewith and whose disclosure is hereby incorporated by reference, represents one such catheter for which the present invention would be particularly useful.

Figure 1:
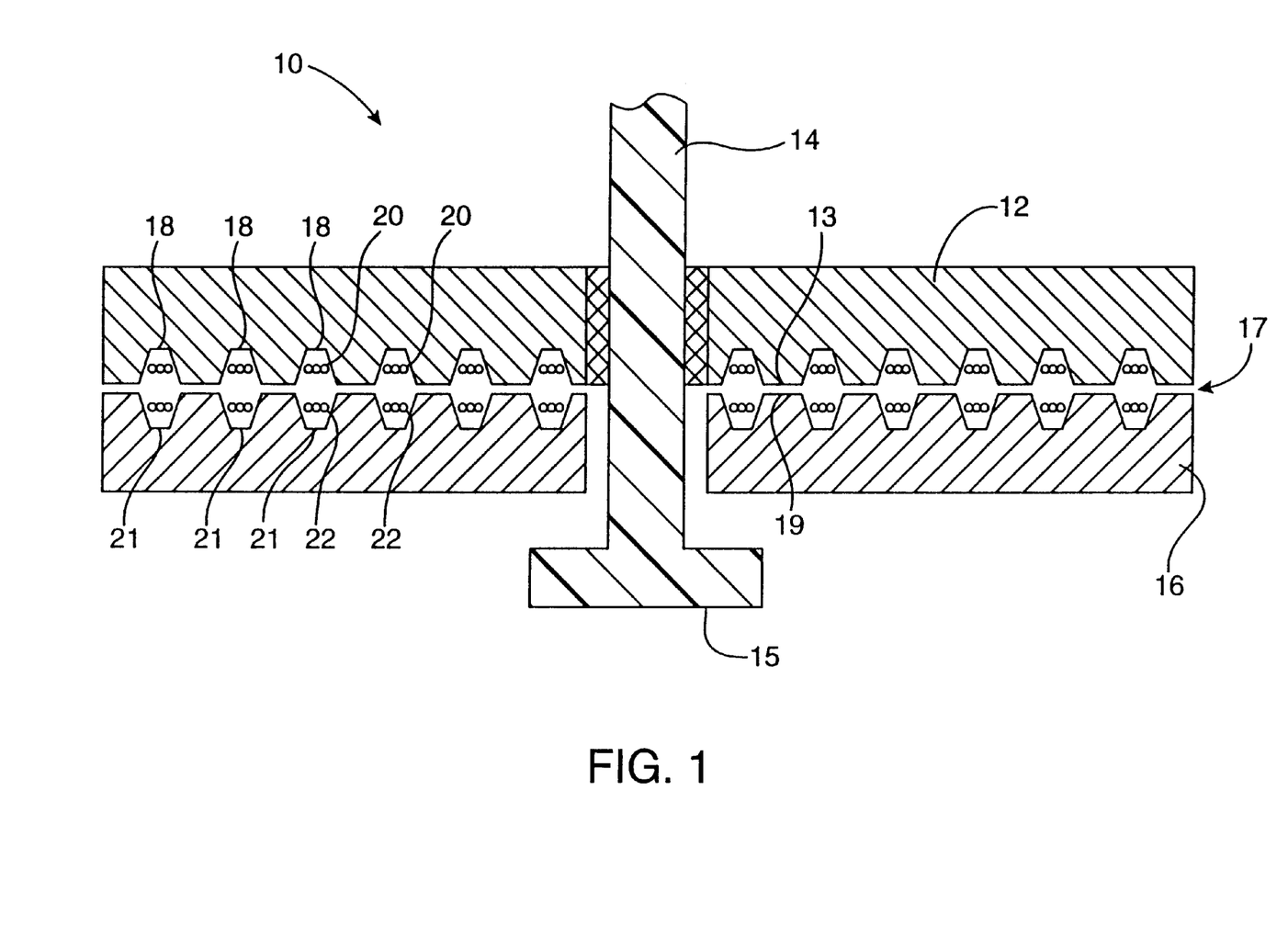
FIG. 1 is a cross-sectional view of a rotary transformer according to the present invention.

Turning now to FIG. 1, a rotary transformer 10 according to the present invention will be described. Rotary transformer 10 comprises a transformer rotor 12 operably attached to a rotary shaft 14. The transformer rotor 12 includes a series of concentric slots or channels 18 located on a proximal side 13 of transformer rotor 12. Each slot 18 contains a number of rotor coils 20. Rotor coils 20 are preferably made from copper wire. Rotor coils 20 also may be made from other conductive wire, such as wire made from silver, gold or the like. Transformer rotor 12 preferably comprises ferrite to facilitate the transfer of magnetic fields. Each rotor coil 20 will have a number of windings or turns, preferably, between about two (2) and about five (5) number of turns per coil. The rotary transformer 10 further comprises a stator 16, also preferably made of ferrite material. A distal side 19 of stator 16 includes a series of concentric slots 21, each containing stator coils 22. The stator coils 22 preferably have between about two (2) and about five (5) number of turns per coil and are preferably made from copper wire. Stator coils 22 may also comprise silver wire, gold wire, or the like. As further discussed in conjunction with FIGS. 2A and 2B, the position of the rotor 12 and stator 16 can be switched, provided that the facing sides of rotor 12 and stator 16 contain the rotor coils 20 and stator coils 22, respectively.

During operation of the rotary transformer 10, the stator 16 will be attached to a housing (not shown in FIG. 1) or some other fixed structure. A proximal end 15 of rotary shaft 14 is operably attached to a drive motor (not shown) which causes the rotary shaft 14 to rotate. In turn, rotation of the rotary shaft 14 causes the rotor 12 to rotate with respect to stator 16.

The transformer rotor 12 and stator 16 are separated by a small gap 17, preferably between about 0.002 inches and about 0.005 inches in distance. In addition, the concentric slots 18 in the proximal side 13 of the transformer rotor 12 and the concentric slots 21 in the distal side 19 of the transformer stator 16 are disposed to face one another across the gap 17. The gap 17 between the rotor 12 and stator 16 allows the rotor coils 20 and stator coils 22 to remain in close proximity even during high speed rotation of rotor 12. Hence, during operation of transformer 10, rotor coils 20 and stator coils 22 are magnetically coupled. As a result, an electric signal transmitted to the stator coils 22 will be received by rotor coils 20 due to mutual induction. Likewise, an electric signal can be transferred from the rotor coils 20 to the stator coils 22.

FIG. 1 depicts six slots 18, 21 on the rotor 12 and stator 16. In practice, the number of slots will typically be between about two (2) and about fifteen (15). As a result, a plurality of signals can be transferred between the rotor 12 and stator 16. Hence, one particularly advantageous feature of the present invention is that such a rotary transformer may be employed in a catheter system to accommodate multiple transducer elements and the transmission of multiple transducer signals using a single catheter. The rotary transformer 10 further allows for the transmission of signals between the rotating and stationary system components without the need for physical connections. In this manner, the rotary transformer 10 transfers communication signals between rotating and non-rotating components without the interferences or wear present in systems that use physical contacts between such components.

Figure 2A:
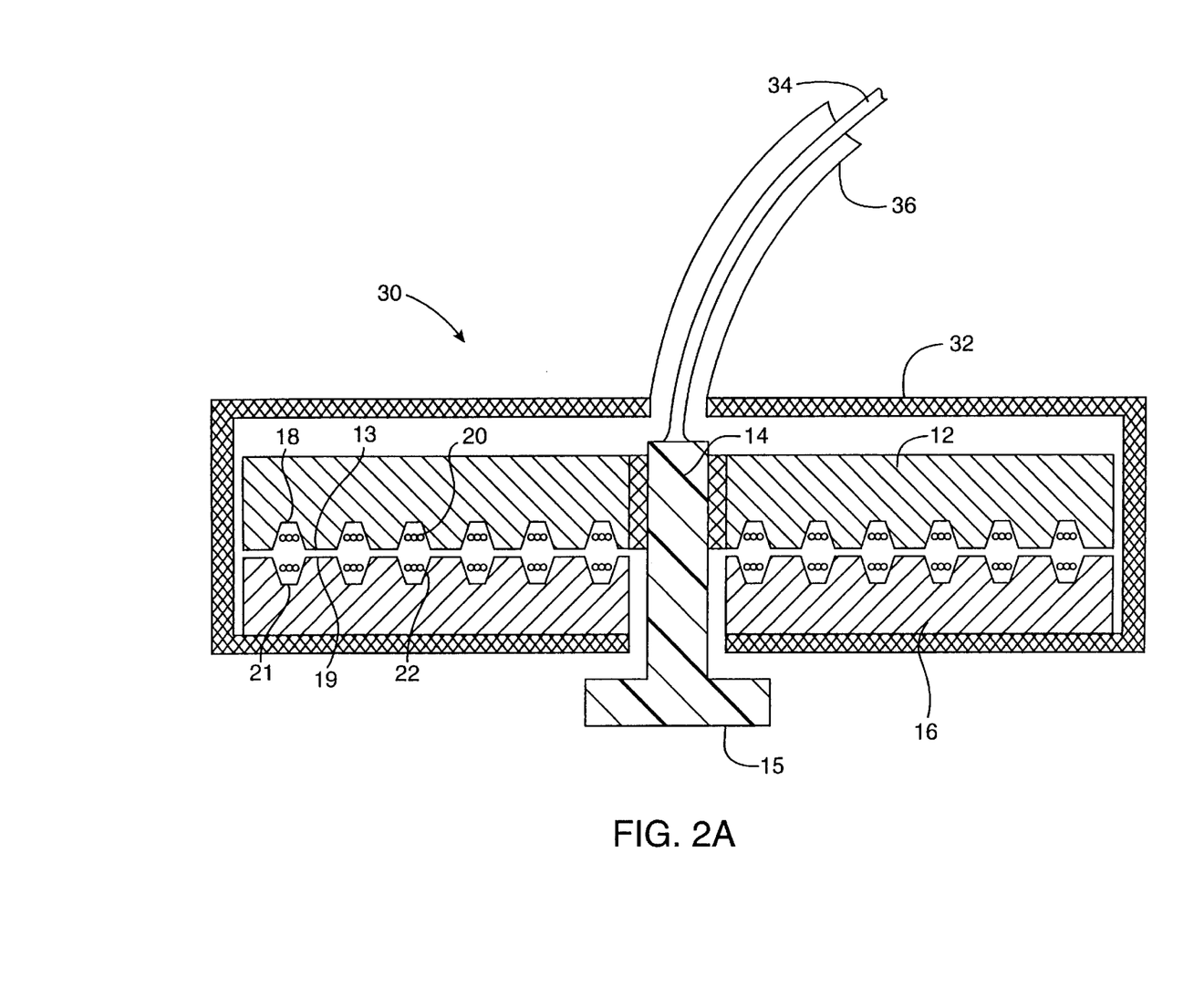
FIGS. 2A and 2B are cross-sectional views of two exemplary catheter systems according to the present invention.

Turning now to FIG. 2A, a catheter system 30 according to the present invention will be described. FIG. 2A depicts the rotary transformer described in conjunction with FIG. 1 coupled to a catheter 36. For convenience of illustration, only a proximal end of catheter 36 is illustrated. As previously described, the rotary transformer comprises rotor 12, stator 16, and rotary shaft 14. Concentric slots 21 located on the distal side 19 of stator 16 and concentric slots 18 located on the proximal side 13 of rotor 12 are configured such that rotor coils 20 are disposed to face stator coils 22. A drive cable 34 is operably attached to the rotary shaft 14. In this manner, rotation of the rotary shaft 14 rotates both the transformer rotor 12 and the drive cable 34. The drive cable 34 is disposed within catheter 36 which may be inserted into a patient. The catheter 36 is configured to be operably attached to a transformer housing 32 in a manner which allows rotation of the drive cable 34 while concurrently producing a stable platform to which the catheter 36 and stator 16 are attached.

Transducers (not shown) are operably attached to the distal end of drive cable 34 and rotate therewith. Transducers for use in the present invention can be made from piezocomposite materials, piezoelectric ceramic materials (such as PZT), piezoplastics, and the like. These transducers are used to convert electrical energy into mechanical energy, which propagates into a body lumen or surrounding body tissues as an ultrasonic signal. The ultrasonic signals are reflected back to the transducers as reflected signals or echoes, which the transducers convert into an electrical signal. Transmission lines operably connect the transducers to the rotor 12, and are preferably disposed inside drive cable 34. Alternatively, the transmission lines can be operably attached to the outside of drive cable 34. In this manner, the reflected signals are transmitted to the rotary transformer 10. Wires or leads (not shown) are used to connect the rotor coils 20 to the transmission lines to facilitate signal transmission.

Figure 2B:
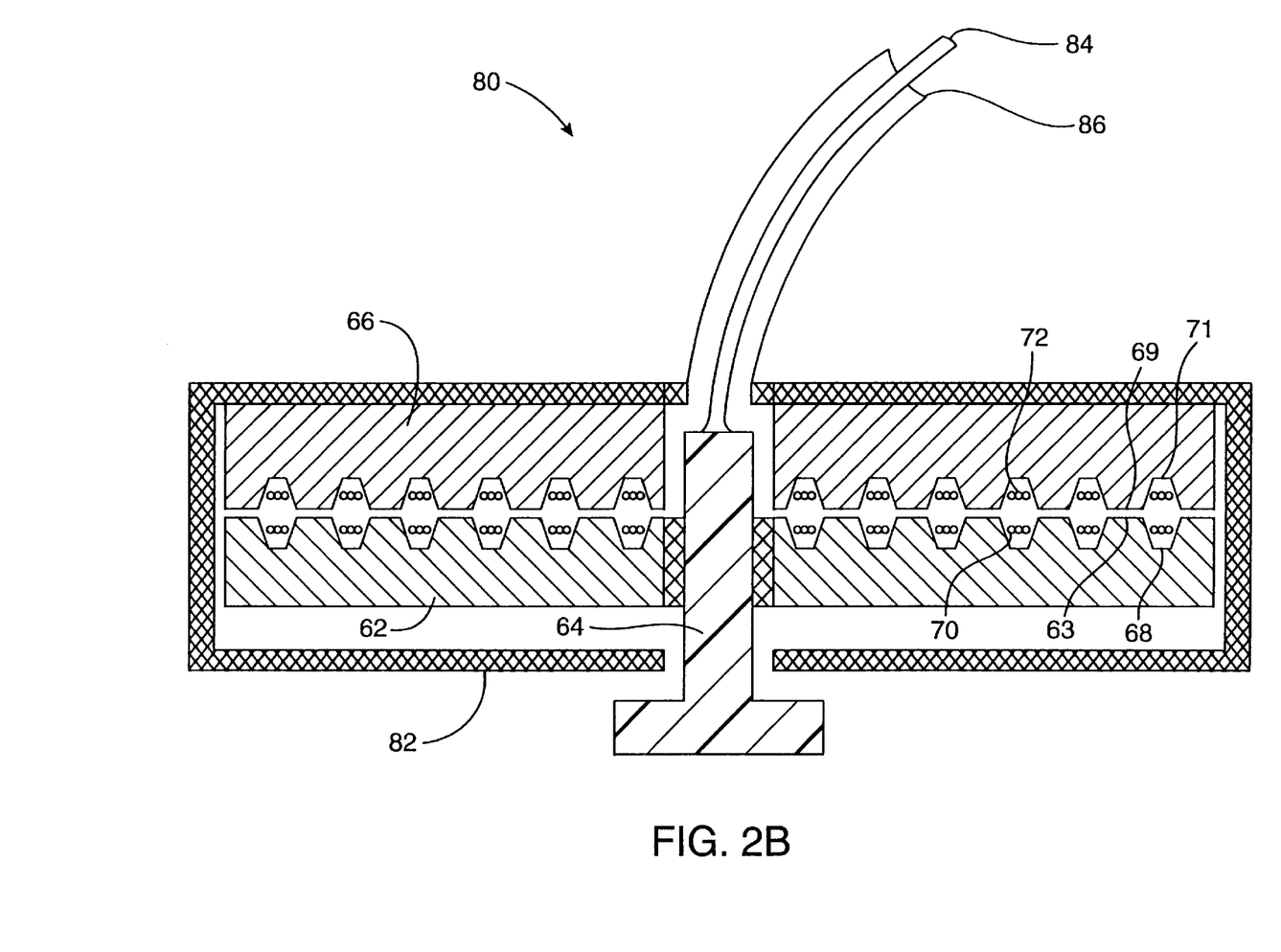

Turning now to FIG. 2B, an alternative embodiment of a catheter system 80 according to the present invention will be described. FIG. 2B depicts a rotary transformer coupled to a catheter 86. For convenience of illustration, only a proximal end of catheter 86 is illustrated. The rotary transformer depicted in FIG. 2B comprises a rotor 62, a stator 66, and a rotary shaft 64. The primary difference between catheter system 30 depicted in FIG. 2A and catheter system 80 depicted in FIG. 2B is the location of the systems' rotors and stators.

Stator 66 includes a plurality of concentric slots 71 located on a proximal side 69 of stator 66 and rotor 62 includes a plurality of concentric slots 68 located on a distal side 63 of rotor 62. Concentric slots 71 contain a number of stator coils 72 and concentric slots 68 contain a number of rotor coils 70, such that rotor coils 70 are disposed to face stator coils 72. A drive cable 84 is operably attached to rotary shaft 64. In this manner, rotation of the rotary shaft 64 rotates both transformer rotor 62 and drive cable 84. Drive cable 84 is disposed within catheter 86 which may be inserted into a patient. Catheter 86 is configured to be operably attached to a transformer housing 82 in a manner which allows rotation of drive cable 84 while concurrently producing a stable platform to which catheter 86 and stator 66 are attached.

Figure 3:
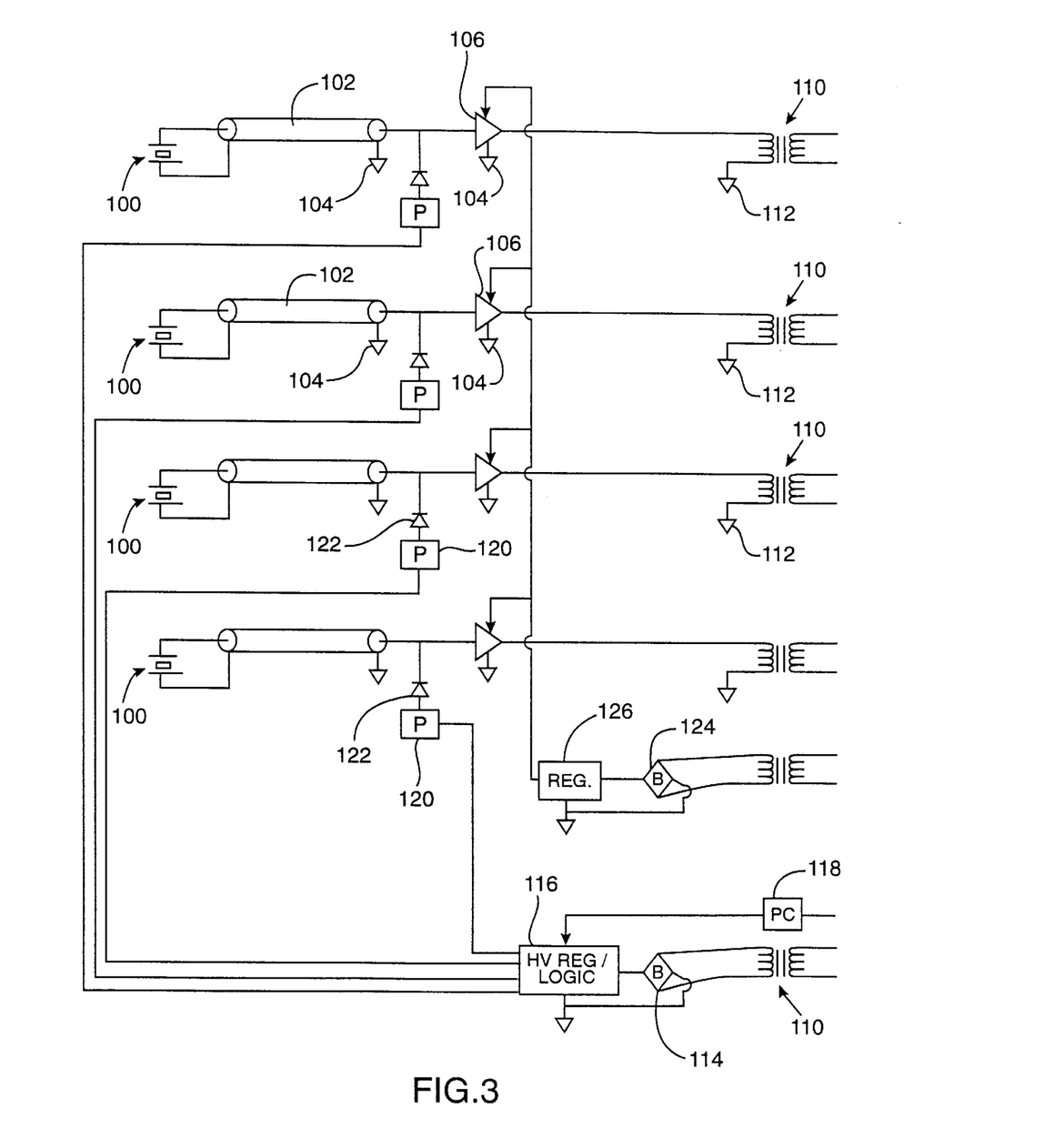
FIG. 3 is a schematic diagram of one embodiment of electronic circuitry that may be incorporated into the catheter systems of FIGS. 2A and 2B.

FIG. 3 depicts a schematic of one preferred electronics that may be used with the catheter systems depicted in FIGS. 2A and 2B. As depicted in FIG. 3, a plurality of transducers 100 are operably attached to a plurality of coaxial transmission lines 102. As noted, the coaxial transmission lines 102 are preferably disposed within a drive cable such as the drive cable 34 depicted in FIG. 2A. Such a configuration allows the transducers and transmission lines to rotate when drive cable 34 rotates. In turn, rotation of the transducers 100 assists the production of ultrasonic images. As depicted in FIG. 3, the coaxial transmission line 102 includes a ground 104 and connects to an amplifier 106 which amplifies an electrical signal returning from the transducer 100. The electrical signal returning from the transducer 100 continues to a transformer tap 110 representing magnetically coupled rotor coils and stator coils. The electrical signal crosses the rotating interface between the transformer rotor and transformer stator. The electric signal is then sent to a controller and image processing equipment (not shown) in order to display an image of the desired region of a patient's anatomy.

The schematic in FIG. 3 depicts four transducer elements, with corresponding transmission lines 102, amplifiers 106 and transformer taps 110. However, it will be appreciated that the number of transducer elements may be larger or smaller than this number depending on the number of transformer taps 110 available for the transmission of electrical signals. Annular arrays such as that disclosed in copending U.S. patent application Ser. No. 09/017,581 (attorney reference number 12553-006300), filed contemporaneously herewith and whose disclosure was previously incorporated by reference, will preferably use between about two (2) and about fifteen (15) transducer elements.

As further depicted in FIG. 3, an additional transformer tap 110 is used to transfer an electric power signal to the rotating side of the transformer in order to power the amplifiers 106. This electric power signal passes through a bridge 124, which converts the signal from alternating current to direct current, and a regulator 126 prior to transmission to the amplifiers 106.

An additional transformer tap 110 is used to transfer high voltage power to a plurality of pulsers 120 located on the rotating portion of the rotary transformer. Such a power signal crosses a transformer tap 110 and passes through a bridge 114 prior to entering a high-voltage regulator/logic circuit 116. The high voltage regulator/logic circuit 116 delivers power to pulsers 120 and coordinates the sequencing of pulses.

During operation of the catheter system, the pulsers transmit an excitation signal or pulse which passes through a diode 122, proceeds down the coaxial transmission line 102 and enters the transducer 100. The excitation pulse will preferably be between about 27 and about 100 volts. Such a pulse allows the transducers 100 to operate. Pulsers 120 in a multi-transducer catheter will preferably operate in series. In other words, a slight time delay exists between pulses emitted by different pulsers. The high voltage regulator/logic circuit 116 preferably contains a logic circuit to coordinate the pulses emitted by pulsers 120. This delay facilitates the receipt of the individual electrical signals returning from the transducers 100. Alternatively, the pulsers 120 can pulse simultaneously, and the receipt of electrical signals in the transducers 100 can be subjected to a differential time delay to facilitate signal processing.

In addition, the pulsers 120 will preferably be controlled to regulate the excitation signal sent to the transducers 100. A control signal is transmitted to the high-voltage regulator/logic circuit 116 by way of a pulser controller 118. Such a pulser controller 118 will transmit the control signal by an additional rotary transformer tap 110, or by other means such as rotary fiber optics, I/D circuits, and the like.

Figure 4:
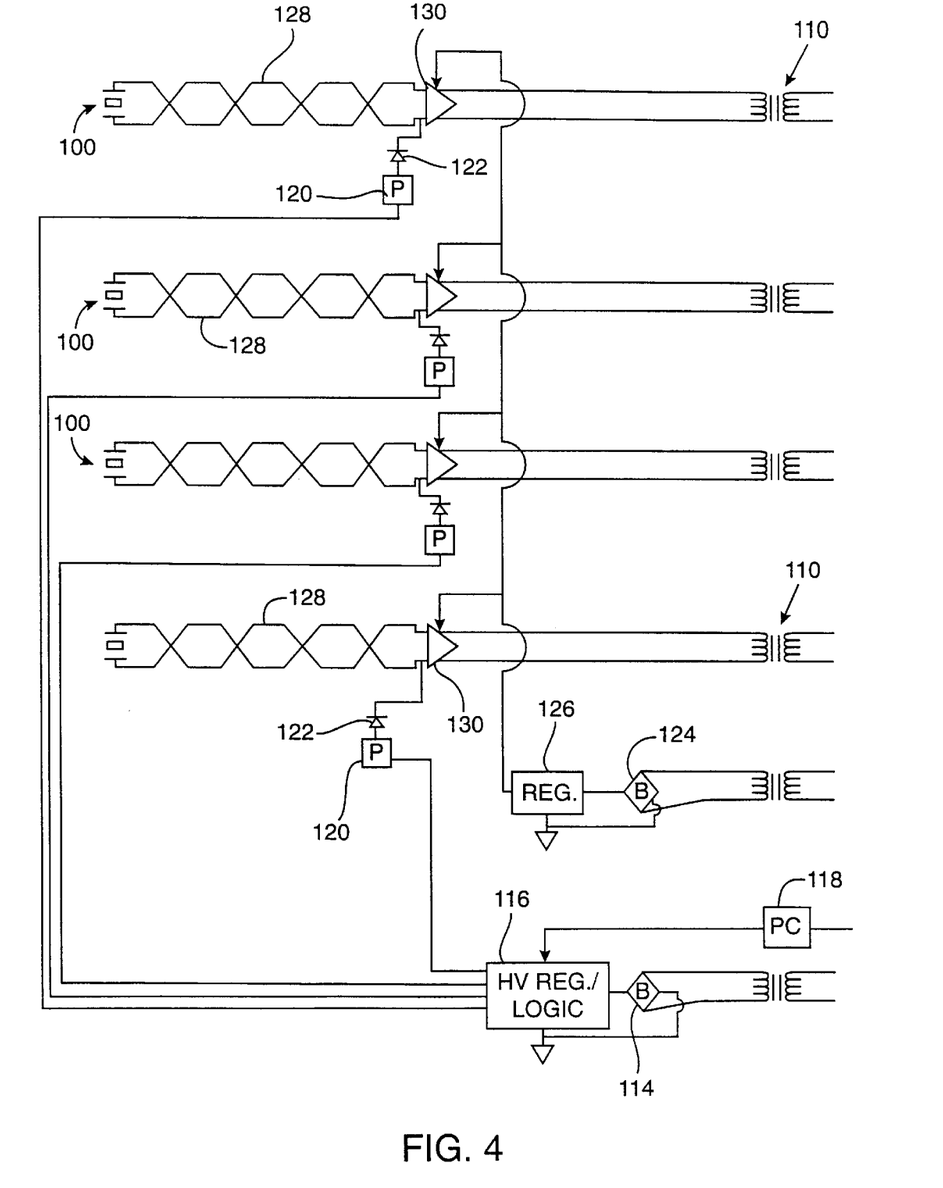
FIG. 4 is a schematic diagram of another embodiment of electronic circuitry that may be incorporated into the catheter systems of FIGS. 2A and 2B.

FIG. 4 provides a schematic of an alternative embodiment of electronic circuitry that may be used with the catheter systems depicted in FIGS. 2A and 2B. One particular distinguishing feature of this embodiment includes the use of a shielded twisted pair transmission line 128. When the catheter system is subjected to external interference up to approximately 100 megahertz (mhz), a shielded twisted pair transmission line provides performance comparable to a coaxial transmission line with a similar outer diameter.

Use of a shielded twisted pair transmission line 128 also allows for a balanced amplifier 130 to be used on the rotating transformer. As with the embodiment described in FIG. 3, electric pulse signals are transmitted to each transducer 100 and return signals from the transducers 100 are transmitted through the amplifiers 130 and across transformer taps 110. Image processing equipment located on the stationary side of the transformer processes the signals to produce an ultrasound image. As in FIG. 3, additional transformer taps 110 are used to provide power across the rotating transformer interface to the amplifiers 130 and pulsers 120.

Figure 5:
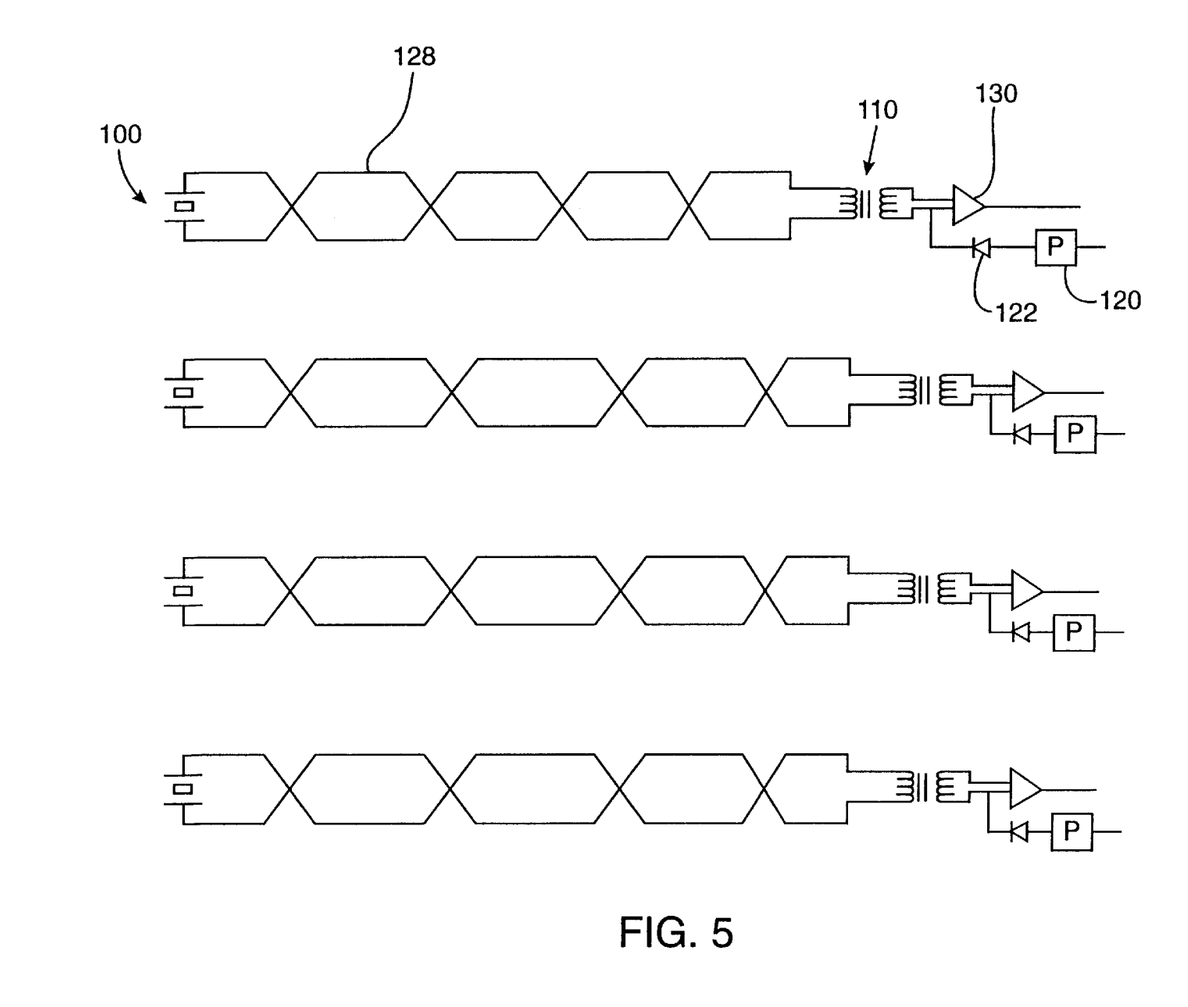
FIG. 5 is a schematic diagram of still another embodiment of electronic circuitry that may be incorporated into the catheter systems of FIGS. 2A and 2B.

FIG. 5 presents a schematic of still another embodiment of electronic circuitry that may be used with the catheter systems depicted in FIGS. 2A and 2B. As depicted in FIG. 5, shielded twisted pair transmission lines 128 are used to transmit signals to and from the transducers 100. In this embodiment, balanced amplifiers 130 are located on the stator side of the rotary transformer. In this configuration, pulsers 120 are also located on the stator side of the transformer and utilize the same transformer taps 110 to send a pulse to the transducers 100 as are used to receive electrical signals from the transducers 100. As previously discussed, image processing equipment is located on the non-rotating side of the rotary transformer. This configuration reduces the amount of hardware and electrical connections on the rotor side of the rotary transformer.

Figure 6:
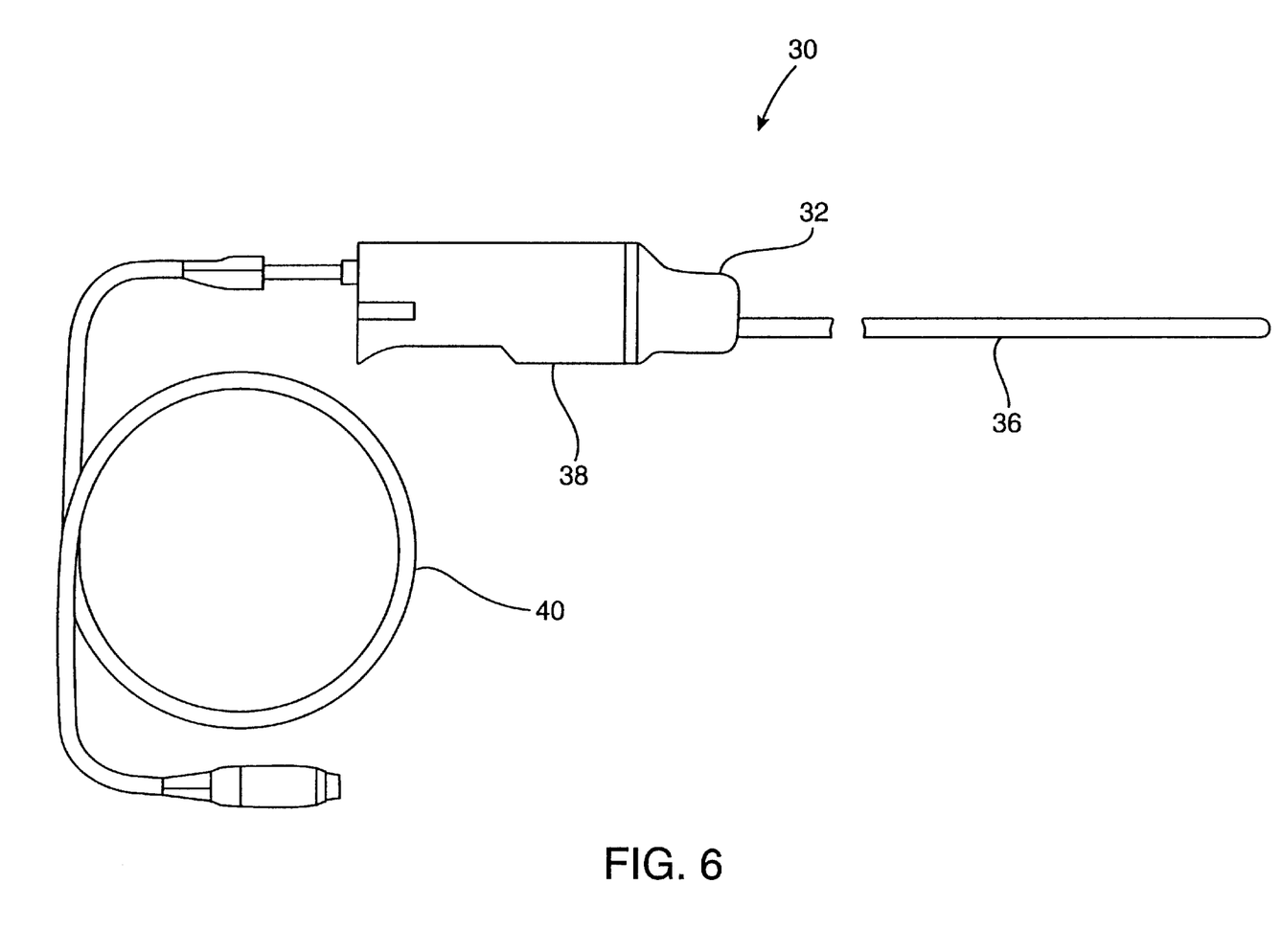
FIG. 6 is a perspective view of a catheter system according to the present invention.

FIG. 6 depicts a perspective view of a catheter system 30 which includes catheter 36 of FIG. 2A. In system 30, catheter 36 is attached to housing 32 within which is contained the rotary transformer (not shown) as previously described. A drive motor 38 is connected to the proximal end 15 of rotary shaft 14 (see FIG. 1) in order to provide rotation of the shaft 14. A controller connection 40 is provided to connect the catheter system 30 to image processing equipment (not shown). As depicted in FIG. 6, the present invention provides the benefit of allowing the electronics to remain outside the patient in a non-disposable system. Such a configuration therefore allows for the reuse of the transformer and accompanying electronics.

Figure 7:
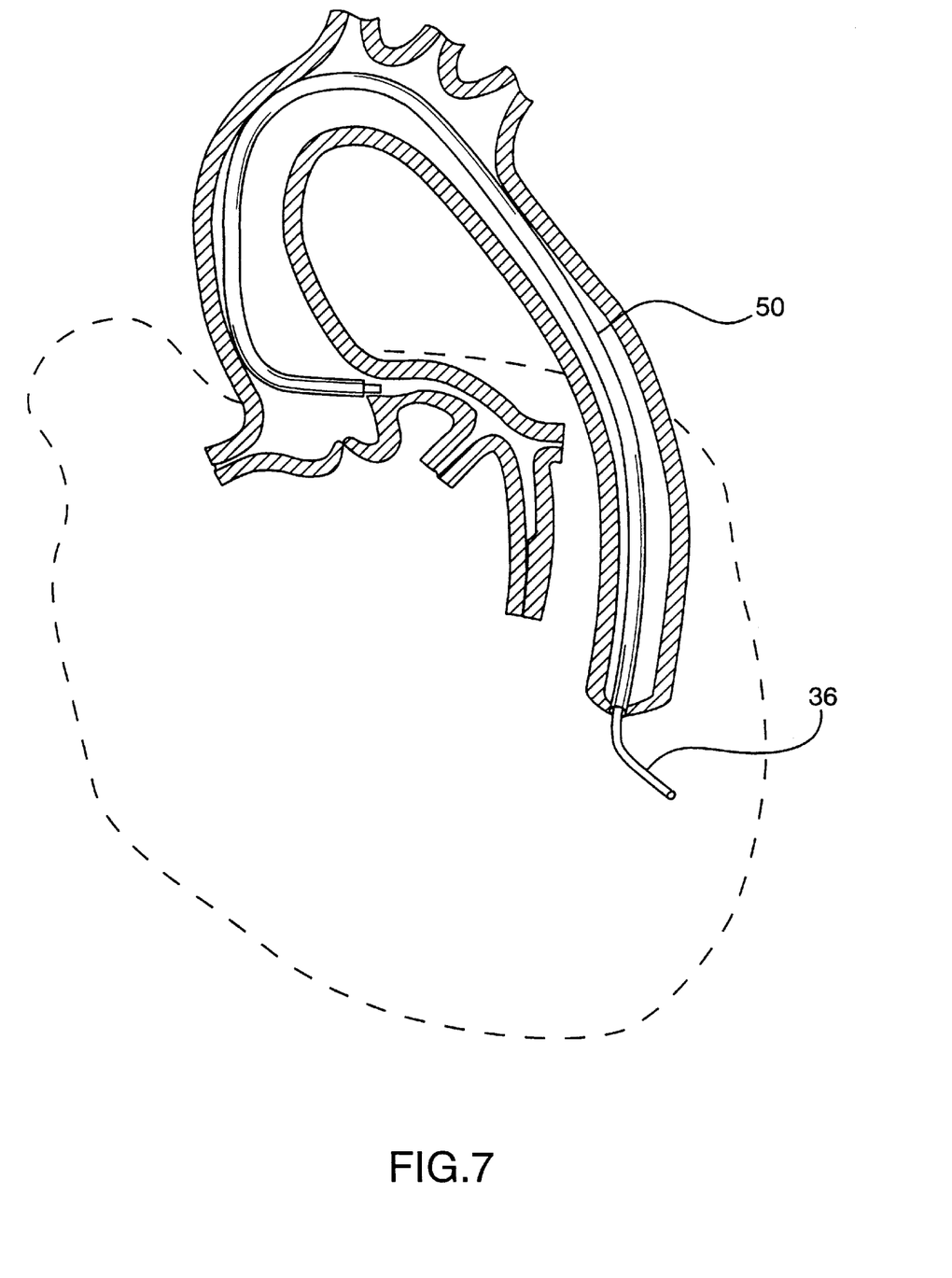
FIG. 7 depicts a catheter according to the present invention inserted into a patient.

FIG. 7 depicts catheter 36 according to the present invention inserted into an artery near a patient's heart. Catheter 36 is preferably inserted through a guide catheter 50 which has been previously positioned to a desired location within the patient. Catheter 36 is then inserted into the patient until the distal end containing the transducers is positioned in an appropriate position within the patient. The cable 34 contained in catheter 36 is rotated, which in turn rotates the transducers 100. The transducers 100 are energized and the transducers capture a reflected signal from the patient. The reflected signal is transmitted across the rotary transformer to a controller and accompanying image processing electronics (not shown). The image processing equipment uses the reflected signal to produce an image of part of the patient's anatomy located near the transducers as is known in the art. Operation of the catheter with a rotary transformer thus allows a multiple transducer catheter system to produce images of the patient.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A catheter system, comprising;
   a catheter comprising an elongate catheter body having a working lumen, a drive cable having proximal and distal ends disposed within the lumen and plurality of transducers attached to the cable near the distal end; and
   a rotary transformer comprising a transformer stator which is spaced apart from a transformer rotor, wherein the rotor is operably attached to the cable near the proximal end to rotate therewith, and wherein the rotor is electrically coupled to the transducers and is magnetically coupled to the stator to allow a signal to be transmitted from at least one of the transducers to the stator during rotation of the cable.

2. A catheter system as in claim 1, wherein the rotary transformer further comprises a plurality of rotor coils mounted in a plurality of concentric slots on a stator-facing side of the rotor, wherein the rotor coils are coupled to the transducers, and wherein the rotor coils are disposed to face a plurality of stator coils mounted in a plurality of concentric slots located on a rotor-facing side of the stator.

3. A catheter system as in claim 2, wherein the rotor is positioned to be proximal relative to the stator.

4. A catheter system as in claim 2, wherein the rotor is positioned to be distal relative to the stator.

5. A catheter system as in claim 2, wherein the catheter further comprises a transmission line having a proximal end and a distal end, wherein the distal end is operably attached to a transducer and the proximal end is operably attached to the rotary transformer to allow the signal to be transmitted from the transducer to the transformer.

6. A catheter system as in claim 5, wherein the transmission line comprises a coaxial cable.

7. A catheter system as in claim 5 wherein the transmission line comprises a twisted pair cable.

8. A catheter system as in claim 5, wherein the rotor further comprises an amplifier operably attached between the proximal end of the transmission line and the rotor coils.

9. A catheter system as in claim 5, wherein the stator further comprises an amplifier operably attached to the stator coils and wherein the proximal end of the transmission line is operably attached to the rotor coils.

10. A catheter system as in claim 2, wherein the catheter further comprises; a plurality of transmission lines each having a proximal end and a distal end, and a plurality of amplifiers which are operably attached to the rotor coils, wherein each transducer is operably attached to the distal end of one of the transmission lines and wherein the proximal end of each transmission line is operably attached to one of the amplifiers.

11. A catheter system as in claim 1, further comprising a rotary shaft and a drive motor assembly, wherein the rotary shaft couples the rotor to the drive motor assembly, and wherein the drive motor assembly rotates the rotary shaft to rotate the rotor.

12. A catheter system as in claim 11, wherein the proximal end of the drive cable is operably attached to the rotary shaft.

13. A rotary transformer system for use in a catheter system, the catheter system having a catheter with a transducer operably attached thereto near a catheter distal end, the transformer system comprising;
    a transformer stator operably attached to a transformer housing;
    a transformer rotor which is adapted to be operably attached to a catheter proximal end, wherein said rotor is operably attached to a rotary shaft and wherein the rotor is disposed to face the stator;
    a plurality of concentric slots on a rotor-facing side of the stator that are disposed to face a plurality of concentric slots on a stator-facing side of the rotor; and
    a plurality of coils mounted in the concentric slots on the stator and the rotor, wherein the coils mounted on the stator are magnetically coupled to the coils mounted on the rotor.

14. A rotary transformer system as in claim 13, wherein the stator-facing side of the rotor is a distal side of the rotor and the rotor-facing side of the stator is a proximal side of the stator.

15. A rotary transformer system as in claim 13, wherein the stator-facing side of the rotor is a proximal side of the rotor and the rotor-facing side of the stator is a distal side of the stator.

16. A rotary transformer system as in claim 13, wherein the rotor and the stator each comprise ferrite.

17. A rotary transformer system as in claim 13, wherein the coils comprise copper wires.

18. A rotary transformer system as in claim 13, wherein the rotor is rotatable relative to the stator to allow a communications signal to be transferred across a gap between the rotor and the stator during rotation of the rotor.

19. A method for imaging a body lumen, the method comprising:
    providing a catheter comprising an elongate catheter body having a working lumen, a drive cable having a proximal end and a distal end disposed within the lumen and a plurality of transducers attached to the cable near the distal end, and wherein the proximal end of the drive cable is operably attached to a rotary transformer;
    coupling the catheter to a controller;
    introducing the catheter into a patient to position the transducers within a body lumen;
    energizing at least one of the transducers;
    rotating the transducers while capturing a reflected signal;
    transmitting the reflected signal across the transformer and to the controller; and
    producing an image of the body lumen based on the reflected signal.

20. A method as in claim 19, further comprising transmitting the reflected signal from a transducer to the transformer along a transmission line.

21. A method as in claim 20, wherein said transmitting step comprises transmitting the reflected signal along the transmission line which comprises a coaxial cable.

22. A method as in claim 20, wherein said transmitting step comprises transmitting the reflected signal along the transmission line which comprises a twisted pair cable.

23. A method as in claim 20, wherein the rotary transformer comprises a transformer stator and a transformer rotor, and further comprising rotating the rotor relative to the stator while the reflected signal is transferred across a gap between the rotor and the stator.

24. A method as in claim 23, wherein the providing step further comprises providing a rotary transformer comprising a plurality of coils mounted in a plurality of concentric slots on a stator-facing side of the rotor, wherein the coils are disposed to face a plurality of coils mounted in a plurality of concentric slots located on a rotor-facing side of the stator.

25. A method as in claim 24, wherein the providing step further comprises providing the rotor to be positioned proximal relative to the stator.

26. A method as in claim 24, wherein the providing step further comprises providing the rotor to be positioned distal relative to the stator.

27. A method as in claim 24, wherein said providing step further comprises providing a rotor comprising an amplifier operably attached between the proximal end of the transmission line and the rotor coils, and further comprising the step of amplifying the reflected signal before the reflected signal is transferred across the gap between the rotor and the stator.

28. A method as in claim 19, wherein the providing step further comprises providing a catheter comprising a plurality of transmission lines having proximal ends and distal ends, wherein each transducer is operably attached to the distal end of one of the transmission lines and the proximal ends of the transmission lines are operably attached to the rotary transformer, and wherein the transmitting step comprises transmitting a plurality of reflected signals across the rotary transformer to produce a plurality of images.

29. A method as in claim 19, wherein the energizing step comprises transmitting an energizing signal across the transformer to a transducer.

30. A catheter system, comprising;
    a catheter comprising an elongate catheter body having a working lumen, a drive cable disposed within the lumen, and a plurality of transducers operably attached to the cable; and
    a rotary transformer comprising a transformer stator which is spaced apart from a transformer rotor, wherein the rotor is operably attached to the cable to rotate therewith;
    wherein the rotor is simultaneously electrically coupled to at least some of said plurality of transducers and the rotor is magnetically coupled to the stator to allow a plurality of signals to be transmitted from said plurality of transducers to the stator during rotation of the cable.

31. A catheter system as in claim 30, wherein said plurality of transducers are electrically coupled to said rotor via a plurality of transmission lines disposed in the working lumen.

32. A catheter system as in claim 31, wherein the number of said plurality of transducers is the same as the number of said plurality of transmission lines, and each of said transducers is electrically coupled to said rotor via one of said transmission lines.

33. A method for imaging a body lumen, the method comprising:

provideing a catheter system comprising
a catheter comprising an elongate catheter body having a working lumen, a drive cable disposed within the lumen, and a plurality of transducers operably attached to the cable; and
a rotary transformer comprising a transformer stator which is spaced apart from a transformer rotor, wherein the rotor is operably attached to the cable to rotate therewith;
wherein the rotor is simultaneously electrically coupled to at least some of said plurality of transducers and said rotor is magnetically coupled to the stator;

coupling the catheter system to a controller;

introducing the catheter into a patient to position the plurality of transducers within a body lumen;

energizing the plurality of transducers;

rotating the plurality of transducers while capturing a plurality of reflected signals;

transmitting the reflected signals across the transformer and to the controller; and producing an image of the body lumen based on the reflected signals.

34. The method of claim 33, wherein said providing step further comprises providing said plurality of transducers to be electrically coupled to said rotor via a plurality of transmission lines disposed in the working lumen.

35. The method of claim 34, wherein the providing step further comprises providing a number of said plurality of transducers to be the same as a number of said plurality of transmission lines, and each of said transducers is coupled to one of said transmission lines.

* * * * *